United States Patent [19]

Ahlstrand et al.

[11] Patent Number: 4,968,299
[45] Date of Patent: Nov. 6, 1990

[54] METHOD AND DEVICE FOR INJECTION

[75] Inventors: Bo Ahlstrand, Djursholm; Ebba Florin-Robertsson, Stockholm; Linda Fryklund, Sollentuna; Birger Hjertman, Vällingby; Anders Ström, Saltsjö-Boo, all of Sweden

[73] Assignee: KabiVitrum AB, Stockholm, Sweden

[21] Appl. No.: 212,647

[22] Filed: Jun. 28, 1988

[30] Foreign Application Priority Data

Jul. 2, 1987 [SE] Sweden ................................ 8702735
Apr. 15, 1988 [SE] Sweden ................................ 8801405

[51] Int. Cl.$^5$ ............................................. A61M 37/00
[52] U.S. Cl. ...................................... 604/90; 604/56; 604/224; 604/232; 604/191
[58] Field of Search ........................ 604/82, 89, 90, 91, 604/56, 224, 232, 234, 191, 416, 211, 208; 222/136, 145

[56] References Cited

U.S. PATENT DOCUMENTS

| | | |
|---|---|---|
| 1,709,691 | 4/1929 | Steuer . |
| 1,750,272 | 3/1930 | Kirk ................................ 604/224 |
| 1,943,120 | 1/1934 | Kabnick ............................ 604/90 |
| 2,345,302 | 3/1944 | Smith ............................. 604/224 |
| 2,549,417 | 4/1951 | Brown . |
| 2,607,344 | 8/1952 | Brown . |
| 2,646,798 | 7/1953 | Brown ............................ 604/234 |
| 2,665,690 | 1/1954 | Lockhart ......................... 604/416 |
| 2,717,601 | 9/1955 | Brown . |
| 3,343,539 | 9/1967 | Moorhouse ..................... 604/224 |
| 3,467,097 | 9/1969 | Ogle ............................... 604/416 |
| 3,811,441 | 5/1974 | Sarnoff .......................... 604/232 |
| 4,226,236 | 10/1980 | Genese . |
| 4,592,745 | 6/1986 | Rex et al. ....................... 604/224 |
| 4,599,082 | 7/1986 | Grimard ......................... 604/90 |
| 4,613,326 | 9/1986 | Szware . |
| 4,648,532 | 3/1987 | Green ............................ 222/136 |

FOREIGN PATENT DOCUMENTS 0278032  5/1964  Australia ........................... 604/56
0207544  7/1987  European Pat. Off. .

Primary Examiner—C. Fred Rosenbaum
Assistant Examiner—Denise W. DeFranco
Attorney, Agent, or Firm—Pollock, Vande Sande & Priddy

[57] ABSTRACT

A dual-chamber cylinder ampoule is used for the mixture of a sensitive, solid medicament, with liquid which is caused to flow calmly through the medicament in order to avoid any shaking and mechanical influence. The mixing is preferably carried out at a pressure above atmospheric.

An injection device for the preparation of an injection solution and a following injection of such solution includes first and second tubular members for enclosing and holding a dual-chamber cylinder ampoule, in which the dry medicament is kept separated from the liquid. When the two tubular members are being screwed together the liquid is calmly and gently mixed with the dry medicament and dissolves it, and the resulted solution can thereafter be injected by means of the dosage and administration mechanism, provided in one tubular member, through a needle arranged at the front end of the other tubular member.

11 Claims, 5 Drawing Sheets

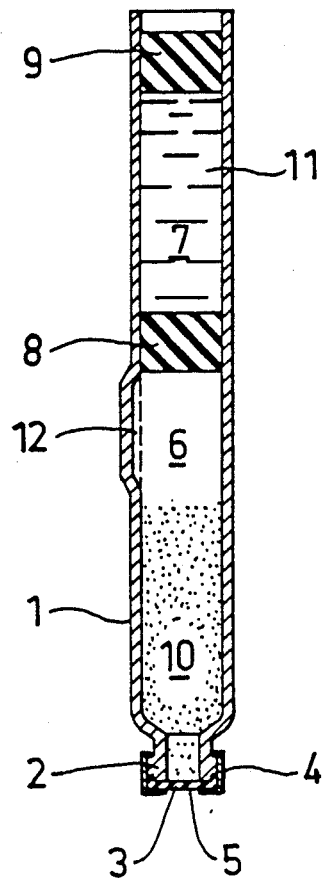
FIG.1
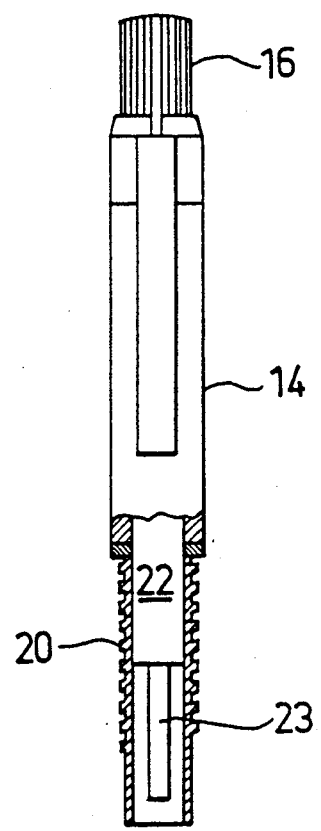
FIG.4
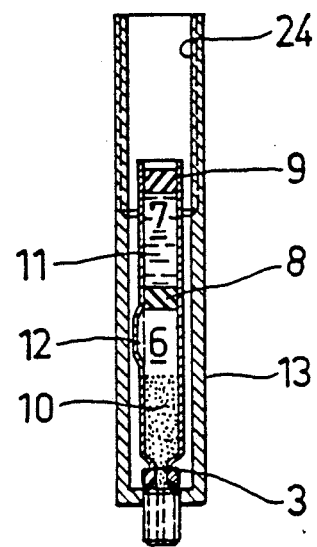

FIG. 2
FIG. 3
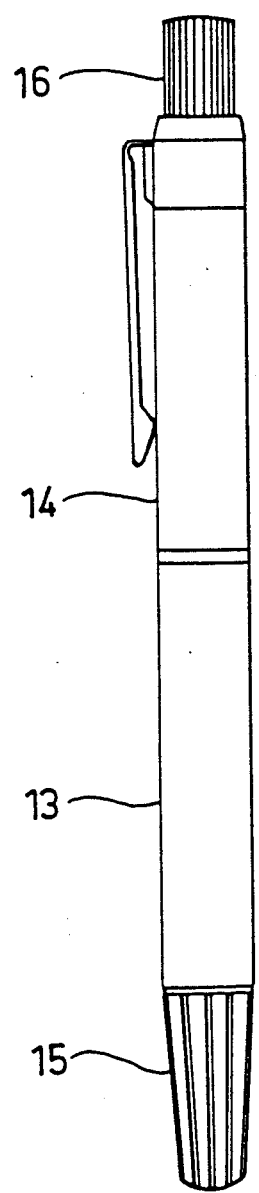
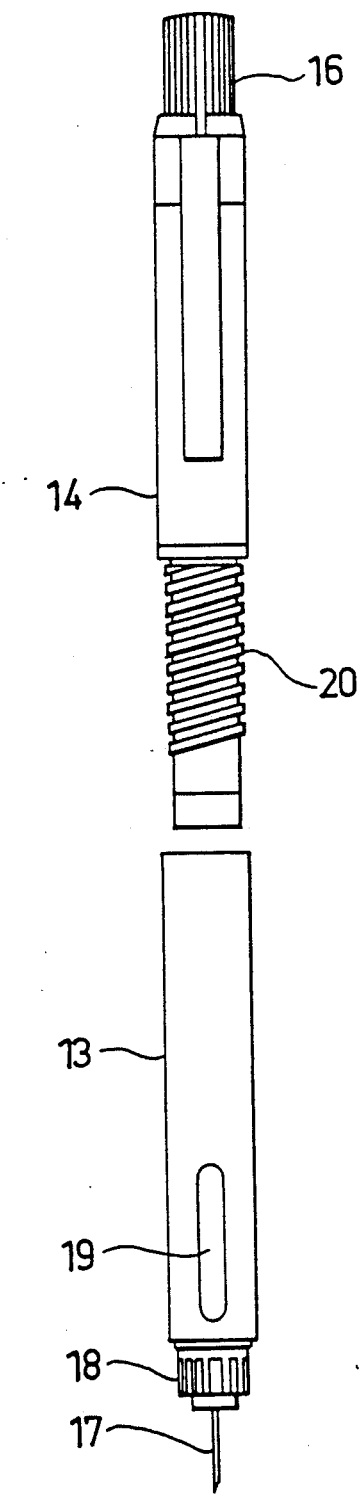

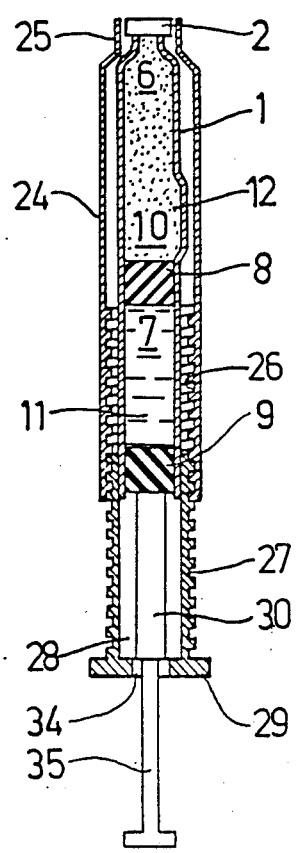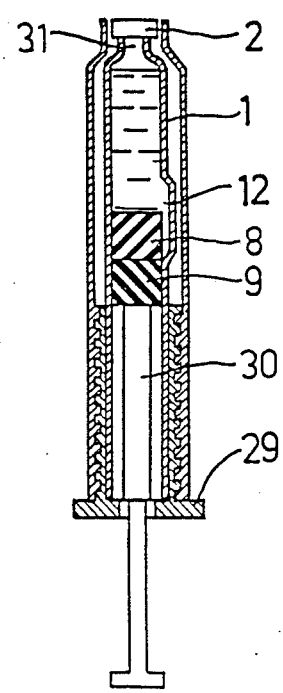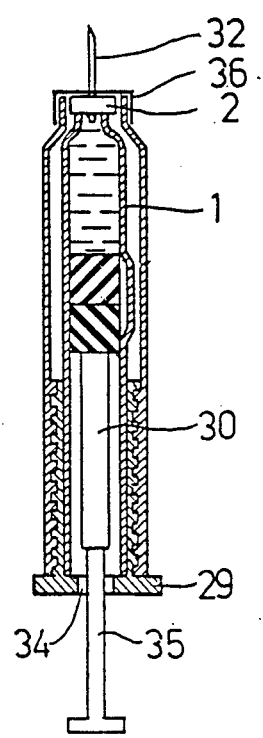

METHOD AND DEVICE FOR INJECTION

BACKGROUND OF THE INVENTION

This invention relates to a method and a device for injection, especially for use in ambulatory treatment. More specifically, the invention relates to a method and a device by means of which an injection solution of a substance is prepared immediately before the injection, or in the preparation of several doses, before the first injection.

Injection devices for use in ambulatory treatment where the medicament is present in a solution are previously known and have been widely used in, for example, insulin treatment of diabetes. Such devices are usually built such that the patient himself can easily assemble a cylinder ampoule for one or more doses, and injection needle and a dosing device in a suitable holder and thereafter give himself easily the required injection. In the device it is also easy to exchange used ampoules and needles for new ones. In an assembled state, such injection devices are often shaped like a fountain-pen and can be easily brought along by the patient.

Moreover, so-called dual-chamber or mixing containers or cylinder ampoules are also known for preparation of solutions of sensitive substances immediately before the injection. Such containers are divided into two chambers separated by a movable wall or piston. The sensitive medicament is present in the front chamber in a dry, usually freeze-dried state and the front end of the front chamber is sealed by a wall penetrable to an injection needle. The liquid intended to dissolve the sensitive substance before the injection is present in the rear chamber. The two chambers are separated by a front movable wall and the rear end of the rear chamber is sealed by means of a rear movable wall. Furthermore, in the container wall there is arranged a connecting passage which can connect the front and the rear chambers.

In a storage position before the injection, there is no communication between the front and the rear chambers. The inlet as well as the outlet of the connecting passage end in the front chamber.

When the container is to be readied for injection, the rear, movable wall in the rear chamber is moved forwards, and due to the incompressibility of the liquid, the front movable wall will then also be moved forwards until it reaches a position just opposite the connecting passage in the wall of the container. When the rear movable wall thereafter is moved further forwards, the liquid will be pressed through the overflow passage into the front chamber where it will be brought into contact with the medicament and dissolved. At the injection the two walls will act together as a piston and press the prepared injection solution out through a needle introduced through the front end wall in the front chamber.

In certain cases the medicament can be so sensitive that special measures must be taken to protect the substance against mechanical influence at the time of dissolution as well as in the further handling of the solution. This applies for example to freeze-dried growth hormones where even a simple shaking of the substance and the liquid can lead to a non-acceptable biochemical change. The preparation of the container for injection must then be made with the utmost carefulness.

It would be very desirable to have available an injection device that is as easy to bring along and handle as those previously known for simple cylinder ampoules in which the medicament is present in a liquid state as a solution, suspension or emulsion, at the same time as the advantages of mixing containers at injection of sensitive substances might be utilized. This object is now achieved by the present invention.

SUMMARY OF THE INVENTION

According to the invention there are provided a method and a device for preparation of an injection solution of one or more substances sensitive to degradation, and a subsequent injection of this solution.

It is intended by the method of the invention to prepare a solution, emulsion or suspension in water of one or more sensitive medicaments for one or more subsequent injections, using a multi-chamber cylinder ampoule known in the art which comprises a front space containing the sensitive medicament and is sealed at its front end by means of a membrane penetrable to an injection needle and delimited at its rear end by a front movable wall, a rear space containing an aqueous phase and which is delimited at its front end by the front movable wall and is delimited at its rear end by a rear movable wall, and a connecting passage arranged in the wall of the ampoule between the rear and the front space, the rear movable wall being moved forwards and entraining thereby the aqueous phase and the front, movable wall until this is just opposite the overflow passage so that the aqueous phase upon continued forward motion of the rear movable wall will flow past the front movable wall into the front space and dissolve, emulsify or suspend the medicament. What characterizes the method is that the aqueous phase is made to flow calmly from below and upwards through the medicament avoiding any shaking and admixture of air.

Moreover, the invention comprises a device for carrying out the present method. What characterizes the device is that it comprises (a) a container for the constituents of the injection solution, in which the constituents are kept separated but can be brought together, by external action, to be mixed and dissolved, and which is made as a tube which is sealed at its front end by means of a penetrable membrane, which in a space between the penetrable wall and a front movable wall contains the solid constituents of the injection solution, in a space between the front movable wall and a rear movable wall contains the liquid constituents of the injection solution and wherein the tubular wall is provided with a connecting passage so arranged, that when the rear movable wall is moved forwards together with the liquid and the front movable wall, the liquid can flow past the front movable wall and be mixed with the solid constituents to a solution;

(b) holder means in which the container can be fixed such that the constituents of the injection solution are brought together and mixed and which is made of two tubular members which can be screwed together and enclose the container such that when the members are screwed together the front end of the container with the penetrable membrane is exposed at the front end of the holder means for penetration by an injection needle and the rear movable wall at the rear end of the container is moved forwards together with the liquid and the front movable wall such that the liquid is made to flow through the connecting passage over to the space of the solid constituents, to be mixed with these to a solution;

(c) holder means for an injection needle arranged to be applied to the front end of the holder means of the container so that the needle can be connected with the interior of the container through the penetrable membrane; and (d) a dosing device connected to the holder means of the container, through the operation of which the rear movable wall in the container is made to be displaced forwards in a controlled way administering determined doses of the injection solution, the dosage device being brought to a starting position for dosage when the holder means of the container are screwed together.

The invention also comprises a more universally useful device for preparation of an injection solution of constituents placed in a container according to point (a) above.

In the following, the invention is described in greater detail with reference to the accompanying drawing.

An embodiment of a device according to the invention is shown in the drawing, wherein:

BRIEF DESCRIPTION OF THE DRAWINGS

FIG. 1 shows a dual-chambered cylinder ampoule having two chambers for use in an injection device;

FIG. 2 is a general view of an injection device according to the invention;

FIG. 3 shows the same device in its disassembled state;

FIG. 4 is a sectional view of the device in its disassembled state;

FIG. 9 is a schematic view of a second embodied variant of the device according to the invention in a position before the preparation of the injection solution;

FIG. 10 is a schematic view of the device shown in FIG. 9 after the preparation of the injection solution; and FIG. 11 is a schematic view of the device according to FIGS. 9 and 10 with applied cannula and ready for injection.

DETAILED DESCRIPTION OF THE PREFERRED EMBODIMENTS

Figure 5:
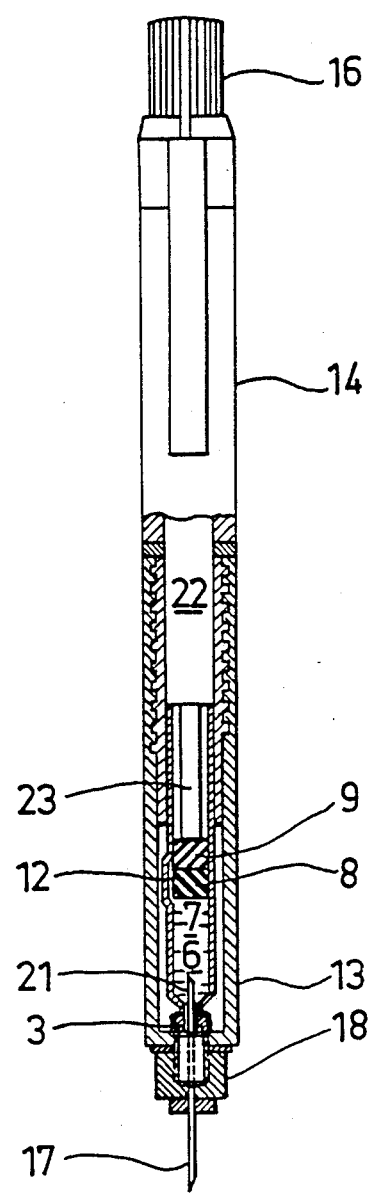
FIG. 5 shows the device ready for injection.

A sectional view of a dual-chamber cylinder ampoule for use in an injection device according to the invention is shown in FIG. 1. The ampoule consists of a tube 1, preferably of glass or a plastic material, which is formed as a bottle-neck with a flange 2 at its front end. The front end is sealed by means of a membrane 3 of rubber or a suitable plastic material which is secured by means of a metal capsule 4. The capsule 4 has an aperture 5 at its central portion so that the membrane 3 is uncovered there. The edge portion of the capsule is further bent around the flange 2 so that the membrane 3 is secured against the front aperture of the ampoule.

The ampoule is divided into a front space 6 and a rear space 7 by means of a movable partition 8. The rear end of the ampoule is sealed by the movable wall 9 which, thus, also seals the rear chamber 7. The two movable walls 8 and 9 can be moved forwards in the ampoule with sealing against the ampoule wall, the ampoule having a substantially circular-cylindrical shape for this purpose.

The front chamber 6 of the ampoule contains one or more medicaments 10 in a dry state, preferably freeze-dried. In this form, also sensitive substances have a relatively good stability. The rear chamber 7 contains a liquid phase 11 which is intended to dissolve the dry injection substance. This liquid phase usually consists of water or a physiological saline solution, and such auxiliary substances as are usual in pharmacological practice can be added to it.

In the wall of the ampoule, connecting passage 12 in the form of a recess is arranged and extends substantially in the longitudinal direction of the ampoule. The overflow passage 12 is located such that it is completely in the front space 6 before the ampoule has been readied for injection and has such a length that it enables a flow past the movable wall 8.

FIG. 2 shows the injection device of the present invention in an assembled state where it can be easily carried along by the patient. The device is generally shaped as a fountain-pen and consists of a front casing portion 13 which encloses a dual chamber cylinder ampoule according to FIG. 1 for the agent to be injected, a rear casing portion 14 enclosing a mechanism for dosage and administration of the agent and a protective cap 15 over the injection needle. The mechanism for dosing and administering the agent is made in any one of several ways known in the art and is not described here in greater detail. Usually it works in such a way that the control knob 16 at the rear end of the device is turned so that an index is set against a scale, a suitable dose being determined. In administration, the control knob is thereafter pushed in, whereby the set dose is administered through the needle. Many different embodiments of such a mechanism for dosage and administration are previously known and can be used in the injection device of the present invention.

FIG. 3 shows the injection device in its disassembled state. Here the protective cap 15 has also been removed so that the front portion 17 of the needle with its holder means 18 is shown. The needle can be screwed onto the front end of the front casing portion 13 by means of the holder device and can be easily replaced. The protective cap 15 should then be applied all the time so that sterility is maintained, and should not be removed until immediately before the injection. An aperture 19 is also made in the front casing portion 13 through which the user can easily control whether any ampoule is inserted and how much is left of the injection solution.

The rear casing portion 14 can be screwed into the front case portion 13 by means of the thread 20. Simultaneously with this screwing an inserted dual-chamber cylinder ampoule for injection is readied, as will be described more closely in the following.

FIG. 4 is a view partly in longitudinal section of the disassembled injection device according to FIG. 3. Here it is apparent that a dual-chamber cylinder ampoule of the type shown in FIG. 1 has been inserted into the front case portion 13 and moved so far that its membrane 3 has been uncovered to be penetrated by the needle. In the rear case portion 14 the dosage and administration mechanism is schematically indicated at 22. This mechanism is provided with a forwardly directed operating rod 23. By its actuation the dual-chamber cylinder ampoule is first readied for injection and determined doses of the injection agent can thereafter be administered with the aid of the control knob 16.

The rear casing portion 14 can be screwed into the front casing portion 13 by the external thread 20 engaging the internal thread 24.

FIG. 5 shows the device assembled and ready for injection. Here the rear movable wall 9 has been moved so far that it has got into contact with the front movable wall 8. This has been brought so far that it has got just opposite the connecting passage 12 and the liquid phase 11 has then flowed past the front movable wall 8 and been mixed with the dry medicament. The pointed rear end 21 of the needle has also been introduced through the membrane 3. The two movable walls 8 and 9 are in contact with each other and have been moved so far that all air in the front space 6 has been expelled through the needle. The device is now ready for injection.

The function of the device when being readied for injection is as follows:

In the rear casing portion 14, the operating rod 23 and the control knob 16 of the dosing and administering mechanism 22 is first set to a starting or zero position. This is done in a way as determined by the design of the mechanism known in the art. The rear casing portion 14 is thereafter screwed into the front casing portion 13 until the operating rod 23 is resting lightly against the rear movable wall 9 in the dual-chamber cylinder ampoule.

When the rear casing portion is screwed in further, the operating rod will push the rear movable wall 9 forwards in the cylinder ampoule, and as the liquid 11 in the rear space 7 is substantially incompressible, the front movable wall 8 will also be pressed forwards. A certain overpressure in the front chamber 6 will arise as air cannot escape.

When the front movable wall 8 has been pushed so far that it is just opposite the overflow passage 12 a liquid connection will be established between the front and the rear chambers. By the further forward motion of the rear movable wall 9 the liquid 11 will then be urged into the front chamber 6 through the overflow passage 12. At this stage, the front movable wall 8 will not move.

When all liquid has been urged into the front space, the rear movable wall 9 will get into mechanical contact with the front movable wall 8. The liquid will now dissolve the dry medicament 10 forming an injection solution ready for use. The holder 18 with the attached needle 17 is thereafter screwed onto the front case portion 13, the membrane 3 of the cylinder ampoule being penetrated by the rear needle tip 21, and the overpressure in the front chamber is released.

By pushing the control knob 16 fully home, the operating rod 23 is actuated so that the walls 9 and 8 are moved further forwards and air in the cylinder ampoule will exit through the needle 17. The device is now ready for injection, as shown in FIG. 5.

When readying the device it is necessary to hold it vertically with the needle end pointing upwards, and the screwing together must not be carried out too quickly. In this way the liquid will rise calmly through the dry substance dissolving it, and no vigorous mixing takes place. Such vigorous mixing is unsuitable for many sensitive substances as it may affect the substance.

It is a preferred embodiment that the dual-chamber cylinder ampoule 1 is positioned in the front casing portion 13 and the solid medicament is dissolved before the needle 21 penetrates the membrane 3 of the ampoule. By the overpressure occurring, the tendency of foaming and formation of bubbles is reduced when the liquid and the solid material are mixed, which is less harmful to the medicament. However, for medicaments that are not so sensitive, the needle holder 18 with the needle can be screwed onto the front casing portion 13 before the cylinder ampoule is introduced and the two casing portions are screwed together. The rear tip of the needle will then penetrate the membrane 3 before the solid substance and the liquid are mixed and no overpressure arises in the mixing chamber.

When the device is to be used for the administration of an injection the protective cap over the needle is first taken off. The desired dose is thereafter set by means of the control knob 16 and by depressing the control knob the dose is administered through the needle. Further doses can thereafter be administered as long as there is injection solution left in the cylinder ampoule. After each administration, the needle is usually replaced with a new sterile needle. This can easily be done by screwing off the holder device 18 with the attached needle from the front end of the injection device and a new holder device with needle is screwed on. At the same time the rear pointed end of the needle will penetrate the membrane 3 and provide a lqiuid connection to the interior of the ampoule.

Figure 6:
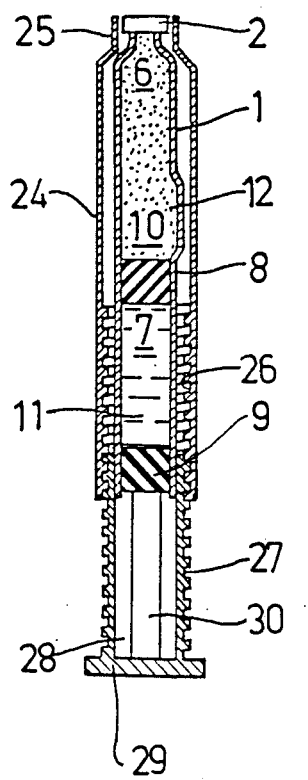
FIG. 6 is a schematic view of a first embodiment of the device according to the invention in a position before the preparation of the injection solution.

Another embodiment of the device according to the invention shown in FIG. 6 comprises a holder means in which the container 1 can be placed. The holder means consists of two substantially tubular members that can be screwed together, viz. a front tubular member 24 and a rear tubular member 28. The front tubular member 24 has a tapering recess 25 at its front end in which the neck ring 2 of the ampoule 1 can be received. At its rear end the front tubular member is provided with an internal thread 26 into which an external thread 27 on the rear tubular member 28 can be threaded. At its rear end the rear tubular member 28 has a closed rear wall 29 to which a fixed piston is attached internally in the rear tubular member 28 which piston has a diameter less than the inside diameter of the ampoule and extends towards the ampoule 1.

In preparation of the injection solution the rear tubular member 28 is threded into the front tubular member 24, the holder means preferably being held vertically with the tapering recess 25 turned upwards. When the rear tubular member 28 is threaded into the front tubular member 24 the fixed piston 30 will move the rear tubular wall upwards compressing the liquid 11 in the rear room 7. The liquid will then exert a pressure on the front wall 8 so that this is moved upwards to a position right in front of the connecting passage 12, in which position the liquid 11 can flow calmly through the connecting passage 12 into the front space 6 and be mixed with the medicament substance 10. As the two tubular members 24 and 28 are screwed together a very calm flow of the liquid into the front space 6 will take place which, moreover, is closed by the membrane at the front end of the ampoule. When the liquid flows into the front space 6 a pressure above atmospheric is formed in this and a small pocket 31 with compressed gas is formed at the top of the ampoule, as is apparent from FIG. 7, which shows the holder means in the position when the two tubular members 24 and 28 are completely threaded into each other and all liquid has streamed into the front space 6. Thanks to the calm inflow of the liquid into the upper space 6 and the pressure above atmospheric formed foam formation in mixing is prevented. Of course the device can thereafter be turned a few times, if required, to dissolve the medicament substance completely in the liquid.

Figure 8:
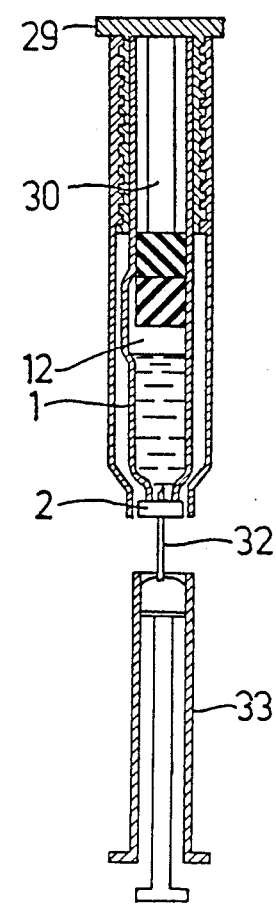
FIG. 8 is a schematic view of the device shown in FIGS. 6 and 7 when taking out the prepared solution into a hypodermic syringe.

When taking out the injection solution prepared in this way the device is turned to the position shown in FIG. 8, thus with the front end of the ampoule 1 turned downwards, the gas in the front space 6 of the ampoule 1 being collected at the top and not close to the membrane. The injection solution can then be taken out with the aid of a cannula 32 which is introduced through the membrane and transferred to a usual hypodermic syringe 33 in a known manner. It is easier to take out the injection solution from the ampoule 1 due to the pressure above atmospheric prevailing in the front space 6 of the ampoule so that the solution at least at the introductory moment will flow by its own pressure through the cannula 32 into the hypodermic syringe 33.

Figure 7:
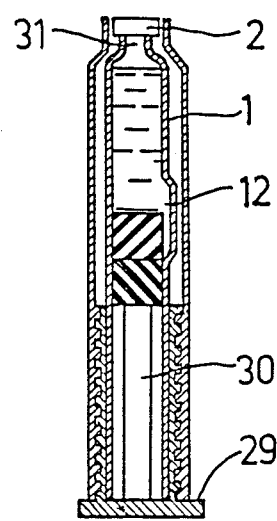
FIG. 7 is a schematic view of the device in FIG. 6 after the preparation of the injection solution.

As previously mentioned a further different embodiment of the device according to the invention is shown in FIGS. 9-11 which, however, has substantially the same constituents as the device shown in FIGS. 6 and 7. The main difference is that the device according to FIGS. 9-11 is designed to be directly provided with a cannula at the tapering recess 25 of the front tubular member 24. Moreover, the rear wall 29 of the rear tubular member 28 is not closed but has a central hole 34 through which an operating rod 35 passes. The operating rod 35 is integrally connected with the piston 30 within the rear tubular member 28, the piston however not being attached to the rear tubular member 28 but restrictedly movable in its longitudinal direction by the aid of the operating rod 35. Like in the device shown in FIGS. 6-8 the outside diameter of the piston 30 is less than the inside diameter of the ampoule 1 but is at the same time larger than the diameter of the hole 34 in the rear wall 29 so that the piston 30 cannot be moved out of the rear tubular member 28. The two tubular members 24 and 28 are screwed together from the position shown in FIG. 9, in which the constituents of the injection solution are quite separated from one another, in the same way as described in connection with the first varied embodiment according to FIGS. 6-8, until a complete mixture has been achieved and the device is in the position shown in FIG. 10. In this position a cover 36 is put onto the tapering recess 25 of the front tubular member 24. Moreover, a cannula 32 is attached to the cover 35 which penetrates the membrane of the ampoule 1 when the cover is put onto the tapering recess 25. This is done in a substantially vertical position with the recess 25 turned upwards. The device is then read for use as a hypodermic syringe, the injection being carried out by pressing in the operating rod 35 so that the piston 30 moves the two movable walls 8 and 9 forwards in the front space 6 in the ampoule and the gas in the ampoule is first removed and so that thereafter the injection solution is fed out through the cannula 32 in known manner.

A very practical and simple instrument for preparation of an injection solution is obtained with the device of the invention. As mentioned above, the device provides a very calm safe mixture of the constituents of the injection solution. If mixing is carried out too quickly the result is particle formation and opalescence. Both are expressions of aggregation. The device is preferably made of a plastic material and in that case the costs of the manufacture of the device will be very low and the device can be used for non-recurrent use. The pitch of the threadable members is not critical but is preferably in the range of 0.5-10 mm.

The device of the invention is preferably used for subcutaneous injection but other injection methods according to current medical practice are also possible, for example intramuscular injection.

When the cylinder ampoule is emptied, the injection device is screwed apart and the empty ampoule is taken out. The dosing mechanism is set to zero and after this the device can be readied again for injection, as indicated above. The screwed-together and readied device can be easily carried along by the user in order to be used at suitable times.

It may be necessary to protect sensitive medicaments, especially of the polypeptide type, against mechanical action when they are in a dissolved form. The moments especially critical are the reconstitution of a dried powder, on one hand, and, on the other hand, the subsequent handling of the prepared solution. The latter will be particularly important when multi-dose preparations are concerned, which must necessarily be handled a number of times.

The use of conventional packages and hypodermic syringes does not give any aid per se to protect against mechanical stresses which, however, this invention does. As the reconstitution of the dried powder by means of the invention is carried out in a very careful way determined by the design, the sensitive medicament is spared. As the solution is prepared at a certain overpressure, foaming and formation of bubbles are also prevented at this stage. The subsequent handling of the prepared solution will also be very gentle in the invention. Practically all air that has been in contact with the solution is removed as the injecting device is readied to give off a first injection from a newly inserted dual-chamber cylinder ampoule. In this way the interface is eliminated which in the handling of the container with solution gives rise to the negative effects on the sensitive medicament, and the container can thereafter be handled without special respect to the sensitive nature of the solution.

Thus it is possible by the present invention to prepare a solution to be used for a long or short time in a gentle way and to transport a prepared solution without degrading the quality of the sensitive medicament due to mechanical stress. Therefore the invention makes it possible that also sensitive medicaments can be made available for a comfortable ambulatory treatment.

The medicaments that can be used in the present device can consist of any substance or mixture of substances used in the previously known dual-chamber ampoules or which are suitable for this use. However, sensitive substances that cannot be stored for a long time in solution and which also have a tendency to be altered when dissolved are especially suitable. Examples of such substances are various polypeptides such as hormones and interferon. The invention has been found to be particularly suitable in the preparation and injection of solutions of growth hormones. These are very sensitive and are easily modified when a solution of them is prepared. By using the present invention in this case, such an influence is considerably reduced. This is extremely surprising and not predictable by one skilled in the art.

Th dry medicaments are usually present in a freeze-dried or lyophilized state before the preparation of the injection solution. The liquid used for the solution usually consists of water to which agents for adjusting the osmotic pressure, preservatives, and the like have often been added in accordance with current pharmacological practice. It is also possible that the liquid phase itself can contain dissolved substances having a pharmacological effect which is then exerted together with the effect of the agent that is later dissolved in the liquid.

Another embodiment is that the liquid can consist of an injectable fat emulsion, for example such a one as is described in U.S. Pat. Nos. 4,073,943 and 4,168,308. In this case the dry injection substance contains a water-soluble or hydrophilic agent which is dissolved or dispersed in the aqueous phase of the emulsion in the mixture.

The injection device is made of some suitable material such as metal, for example stainless steel or light metal or some suitable plastic material. The choice of material is well within the competence of one skilled in the art.

Moreover, it should be noted that the method and device of the invention shown in the drawing and the detailed description are only an example and that other embodiments are also possible within the scope of the claims.

What is claimed is:

1. A method of preparing a solution, emulsion, or suspension in a fluid of one or more sensitive medicaments for one or more subsequent injections using a multi-chamber cylindrical ampoule including at least a first chamber of a variable volume for containing the sensitive medicament, said first chamber being sealed at its front end by a membrane penetrable to an injection needle and delimited at its rear end by a first movable member, and a second chamber formed in said cylindrical ampoule for containing the fluid and being defined at its front end by said first movable member and at its rear end by a second movable member, and a connecting passage arranged in a wall of said cylindrical ampoule between said first and second chambers for providing a communication therebetween, said method comprising the steps of:
   providing a holder member for holding said cylindrical ampoule therein, said holder member including a first and a second part, said first and second part including corresponding threaded means thereon;
   inserting said cylindrical ampoule into one of said parts of said holder member;
   connecting said first and second parts by screwing said corresponding threaded means;
   simultaneously with said screwing, effecting movement of said second movable member with said fluid towards said first movable member for causing movement of said first movable member along the wall of said cylindrical ampoule for opening said connecting passageway;
   continuing screwing of said parts of said holder member whereby a slow, gentle and constant flow of said fluid controlled by the screwing operation is provided from said second into said first chamber for the dissolution, suspension or emulsification of the sensitive medicament in said first chamber.

2. The method according to claim 1, wherein said fluid and said sensitive medicament are brought into contact with one another at a pressure above atmospheric.

3. The method according to claim 1, wherein said membrane is penetrated by the injection needle only after the medicament has been dissolved, emulsified or suspended in said fluid.

4. A method of dissolution of a sensitive solid substance by a liquid substance in a container in which each of said substances is being kept in one of two separate chambers of variable volume, said chambers being capable of passing liquid from said chamber containing said liquid into said chamber containing said sensitive, solid substance through a passageway communicating said chambers upon actuation by an external member, said method comprising the steps of:
   providing an encasing member having two parts, said two parts being connectable through corresponding threaded means;
   positioning said container in one of said two parts of said encasing member;
   applying said two parts of said encasing member for interconnection;
   causing longitudinal displacement of said second chamber filled with said liquid towards said first chamber by means provided in said second part of said encasing member upon screwing movement of said two encasing members to effect movement of said first chamber, whereupon effecting an actuation and opening of a liquid communication between said first and second chamber through said passageway for slowly and gently passing said liquid from said second to said first chamber, the flow of said liquid being steadily controlled by said screwing movement, whereby the mixing and the dissolution of said sensitive, solid substance by said liquid substance is protected against shaking and other mechanical influence.

5. An injection device for the preparation of a solution, emulsion or suspension of a sensitive, solid substance in a fluid and a subsequent injection, with said solid, sensitive medicament and said fluid being kept separately, said device comprising:
   a dual-chamber cylindrical member, with a first chamber for containing said sensitive, solid substance having a bottom defined by a needle penetrable member and a top defined by a first movable member, a second chamber for containing said fluid having a bottom defined by said first movable member and a top defined by a second movable member, and a connecting passage formed in the wall of said cylindrical member for communicating said first and second chambers, said connecting passage being located entirely within said first chamber and closed off from said second chamber by said first movable member and openable upon external actuation; and
   a first and a second tubular member, said tubular members including threaded means for interconnection of said first and second members for encasing said dual-chamber cylindrical member therein, said first tubular member being adapted for holding said cylindrical member therein and having means for exposing said penetrable member to a needle injection;
   said second tubular member housing means for effecting longitudinal movement of said second movable member with said fluid and of said first movable member to open said connecting passageway for passing said fluid from said second to said first chamber upon screwing operation of said two tubular members onto each other, said screwing operation controlling passing of said fluid into said second chamber for dissolution of said sensitive, solid substance, whereby said dissolution and a subsequent handling of the dissoluted substance is maintained in a gentle, slow and lenient manner, preventing any deterioration of the sensitive medicament by mechanical influence.

6. The injection device according to claim 5, wherein said means for effecting longitudinal movement comprises a piston arranged in said other tubular member and wherein said means for exposing said penetrable member includes an opening provided in said one tubular member alignable with said penetrable member.

7. A injection device for the preparation of an injection solution of degradation-sensitive substances and a subsequent injection of the solution, comprising:

a dual-chamber container for separate containing of the constituents of the injection solution and means for bringing the constituents together to be mixed and dissolved, said container including a tubular member being sealed at its front end by a needle penetrable member which defines a bottom of a first chamber with a variable volume, and a first movable member disposed in said tubular member defining a top of said first chamber, said first chamber containing the solid constituents of the injection solution, and a second chamber having a bottom defined by said first movable member and a top defined by a second movable member, said second chamber containing the liquid constituents of the injection solution, and said means for bringing said liquid and solid constituents together including a connecting passage in a wall of said tubular member arranged to be closed by said first movable member in a separated state of said constituents;

holding means adapted for insertion of said dual-chamber container therein, said holding means including a first and a second part, each provided with corresponding threaded means for connecting said first and second parts together;

said needle penetrable member being exposed at a front end of said first part of said holding means for penetration by an injection needle, said second part of said holding means being provided with means for effecting movement of said second movable member towards said first movable member, causing movement of said liquid constituent and of said first movable member for opening of said connecting passageway, upon screwing of said first and second parts onto each other, whereby said liquid constituent flows from said second chamber into said first chamber to mix with said solid constituents, wherein the flow of said liquid is controlled by screwing of said first and second parts; and means for injection of said solution.

8. A device according to claim 7, wherein said means for injection comprising a dosing device connected to said second part of said holding means.

9. A device according to claim 8, wherein said dosing device is brought into a starting position when screwed together with said parts of said holding means, said dosing device being provided with means for effecting said longitudinal displacement of said second movable member.

10. A device according to claim 7, further comprising:

a holder for an injection needle connectable to said front end of said first part of said holding means.

11. A device according to claim 7, wherein said means for injection comprises a plunger rod connected to said means for effecting movement of said second movable member.

* * * * *